US011523903B2

(12) United States Patent
Murray et al.

(10) Patent No.: US 11,523,903 B2
(45) Date of Patent: *Dec. 13, 2022

(54) DELIVERY CATHETER SYSTEM WITH MICRO AND MACRO MOVEMENT CONTROL

(71) Applicant: Medtronic, Inc., Minneapolis, MN (US)

(72) Inventors: Robert Murray, Santa Rosa, CA (US); Sameer Upadhyaya, Santa Rosa, CA (US); Mark Casley, Taylors Hill (IE); Patrick Macaulay, Windsor, CA (US); Ak Masud, Maple Grove, MN (US); Paul Cassidy, Shoreview, MN (US); David Clarke, Ballybrit (IE)

(73) Assignee: Medtronic, Inc., Minneapolis, MN (US)

( * ) Notice: Subject to any disclaimer, the term of this patent is extended or adjusted under 35 U.S.C. 154(b) by 280 days.

This patent is subject to a terminal disclaimer.

(21) Appl. No.: 16/856,767

(22) Filed: Apr. 23, 2020

(65) Prior Publication Data

US 2020/0246144 A1  Aug. 6, 2020

Related U.S. Application Data

(63) Continuation of application No. 15/285,784, filed on Oct. 5, 2016, now Pat. No. 10,639,150, which is a
(Continued)

(51) Int. Cl.
*A61F 2/24* (2006.01)
*A61M 25/00* (2006.01)

(52) U.S. Cl.
CPC ......... *A61F 2/2436* (2013.01); *A61M 25/002* (2013.01)

(58) Field of Classification Search
CPC .......... A61F 2/2436; A61F 2/966; A61F 2/95; A61F 2/962; A61F 2/2427; A61M 2025/09125
See application file for complete search history.

(56) References Cited

U.S. PATENT DOCUMENTS

| 3,186,556 A | 6/1965 | Bo |
| 3,404,818 A | 10/1968 | Constance |

(Continued)

FOREIGN PATENT DOCUMENTS

| DE | 102006039823 A1 | 3/2008 |
| EP | 1731189 | 12/2006 |

(Continued)

OTHER PUBLICATIONS

Merriam-Webster defination for "fixed" accessed Aug. 29, 2019; https://merriam-webster.com/dictionary/fixed (2019).

(Continued)

*Primary Examiner* — Wade Miles
(74) *Attorney, Agent, or Firm* — Medler Ferro Woodhouse & Mills PLLC

(57) ABSTRACT

A tray and packaging system for a prosthetic valve delivery system permits conversion from a storage and/or shipping configuration to a set up and preparation configuration. In a first configuration, a delivery system can be supported by first and second main trays with the elongate catheter of the delivery system arranged to extend linearly from the first main tray to the second main tray, and in a second configuration, the delivery system can be supported by the first and second main trays with the elongate catheter of the delivery system turned back in a U-shaped manner with the deployment portion of the delivery system positioned to the side of the control handle portion of the delivery system.

12 Claims, 11 Drawing Sheets

Related U.S. Application Data continuation of application No. 13/469,676, filed on May 11, 2012, now Pat. No. 9,486,604.

(60) Provisional application No. 61/485,434, filed on May 12, 2011, provisional application No. 61/485,455, filed on May 12, 2011.

(56) References Cited

U.S. PATENT DOCUMENTS

| | | | |
|---|---|---|---|
| 3,851,649 | A | 12/1974 | Villari |
| 4,053,280 | A | 10/1977 | Salisbury |
| 4,128,173 | A | 12/1978 | Lazarus et al. |
| 4,226,328 | A | 10/1980 | Beddow |
| 5,098,391 | A | 3/1992 | Pantages et al. |
| 6,012,586 | A | 1/2000 | Misra |
| 6,619,482 | B1 | 9/2003 | King |
| 6,705,655 | B2 | 3/2004 | Yang |
| 8,226,669 | B2 | 7/2012 | Detruit et al. |
| 8,584,849 | B2 | 11/2013 | McCaffrey |
| 9,144,494 | B2 | 9/2015 | Murray |
| 10,639,150 | B2 * | 5/2020 | Murray ............... A61M 25/002 |
| 2002/0045843 | A1 | 4/2002 | Barker |
| 2005/0027305 | A1 | 2/2005 | Shiu et al. |
| 2007/0197998 | A1 | 8/2007 | Itou et al. |
| 2008/0147182 | A1 | 6/2008 | Righini et al. |
| 2010/0049313 | A1 | 2/2010 | Alon et al. |
| 2011/0054594 | A1 | 3/2011 | Mayberry |
| 2012/0310332 | A1 | 12/2012 | Murray et al. |

FOREIGN PATENT DOCUMENTS

| | | |
|---|---|---|
| EP | 1982677 | 10/2008 |
| WO | WO2009/140971 | 11/2009 |
| WO | WO2011/011023 | 1/2011 |

OTHER PUBLICATIONS

Merriam-Webster defination of "detent" accessed Apr. 17, 2019; https://merriam-webster.com/dictionary/detent.
Merriam-Webster defination of "clamp" accessed Apr. 17, 2019; https://merriam-webster.com/dictionary/clamp.
Merriam-Webster defination of "container" accessed Apr. 17, 2019; https://merriam-webster.com/dictionary/container.
Merriam-Webster defination of "actuator" accessed Apr. 17, 2019; https://merriam-webster.com/dictionary/actuator.
Merriam-Webster defination of "retractor" accessed Apr. 17, 2019; https://merriam-webster.com/dictionary/retractor.
Extended European Search Report in EP application No. 20196173. 7-1113, dated Nov. 30, 2020.

* cited by examiner

DELIVERY CATHETER SYSTEM WITH MICRO AND MACRO MOVEMENT CONTROL

CROSS-REFERENCE TO RELATED APPLICATION

This application is a Continuation of and claims priority to U.S. patent application Ser. No. 15/285,784, filed Oct. 5, 2016, which is a Continuation of and claims priority to U.S. patent application Ser. No. 13/469,676, filed May 11, 2012, which claims the benefit under 35 U.S.C. § 119(e) of U.S. Provisional Patent Application No. 61/485,434, filed May 12, 2011, and U.S. Provisional Patent Application No. 61/485,455 filed May 12, 2011, which are incorporated herein by reference in their entirety.

TECHNICAL FIELD

The present invention relates generally to devices and methods for repair The present invention relates to a delivery system for positioning and deploying a prosthetic heart valve, in particular an aortic heart valve. More specifically, the present invention is directed to aspects of providing the delivery system for use by a surgeon and of controlling the delivery and deployment of such a prosthetic heart valve.

BACKGROUND

Recently, there has been interest in minimally invasive and percutaneous replacement of cardiac valves. In the specific context of pulmonary valve replacement, for example, U.S. Patent Application Publication Nos. 2003/0199971 A1 and 2003/0199963 A1, both filed by Tower, et al. and incorporated herein by reference, describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the native valve leaflets against the right ventricular outflow tract, thereby anchoring and sealing the replacement valve.

As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, both incorporated herein by reference in their entireties, the replacement pulmonary valve may be implanted to replace native pulmonary valves or prosthetic pulmonary valves located in valved conduits. Other articles that describe features of percutaneous valve implantation include Louise Coats, et al., "The Potential Impact of Percutaneous Pulmonary Valve Stent Implantation on Right Ventricular Outflow Tract Re-Intervention," European Journal of Cardio-Thoracic Surgery (England), April 2005, pgs. 536-43; Peter C. Block, et al., "Percutaneous Approaches to Valvular Heard Disease," Current Cardiology Reports (United States), March 2005, pgs. 108-13; Georg Lutter, et al., "Percutaneous Valve Replacement: Current State and Future Prospects," Annals of Thoracic Surgery (Netherlands), December 2004, pgs. 2199-206; Younes Boudjemline, et al., "Percutaneous Pulmonary Valve Replacement in a Large Right Ventricular Outflow Tract: An Experimental Study," Journal of the American College of Cardiology (United States), Mar. 17, 2004, pgs. 1082-7; S. Khambadkone, et al., "Percutaneous Implantation of Pulmonary Valves," Expert Review of Cardiovascular Therapy (England), November 2003, pgs. 541-18; Y. Boudjemline, et al., "Percutaneous Valve Insertion: A New Approach," Journal of Thoracic and Cardiovascular Surgery (United States), March 2003, pgs. 741-2; Philipp Bonhoeffer, et al., "Percutaneous Insertion of the Pulmonary Valve," Journal of the American College of Cardiology (United States), May 15, 2002, pgs. 1664-9; Younes Boudjemline, et al., "Steps Toward Percutaneous Aortic Valve Replacement," Circulation (United States), Feb. 12, 2002, pgs. 775-8; P. Bonhoeffer, et al., "Percutaneous Replacement of Pulmonary Valve in a Right-Ventricle to Pulmonary-Artery Prosthetic Conduit with Valve Dysfunction," Lancet (England), Oct. 21, 2000, pgs 1403-5; P. Bonhoeffer, et al., "Transcatheter Implantation of a Bovine Valve in Pulmonary Position: A Lamb Study," Circulation (United States), Aug. 15, 2000, pgs. 813-6; G. O. Yonga et al., "Effect of Percutaneous Balloon Mitral Valvotomy on Pulmonary Venous Flow in Severe Mitral Stenosis," East African Medical Journal (Kenya), January 1999, pgs. 28-30; and G. O. Yonga, et al., "Percutaneous Transluminal Balloon Valvuloplasty for Pulmonary Valve Stenosis: Report on Six Cases," East African Medical Journal (Kenya), April 1994, pgs. 232-5, all of which are also incorporated herein by reference in their entireties.

The approach to pulmonary valve replacement described in the above patent applications and articles remains a viable treatment for certain patients. In particular, the Melody valve is a commercial form of a pulmonary valve replacement available from Medtronic, Inc. that is usable according to the above noted approach. Other techniques have also been developed to broaden those patients that can benefit from such pulmonary valve replacement procedures including the provision of other size valves than those of sizes that can be created from the size range of available valved segments of bovine jugular veins.

A delivery system that is associated with the Melody pulmonary valve is also commercially available from Medtronic, Inc. The Melody delivery system is a catheter system that includes an inflatable balloon at a distal end of the device onto which the pulmonary valve replacement is crimped. This system is designed for control and steerability from a proximal end of the device for guiding the pulmonary valve replacement to position within a patient's heart via the patient's vasculature. In particular, this system is designed for deployment by the balloon at the patient's native pulmonary valve annulus as accessed via the femoral vein of the patient. The valve is typically sheathed as crimped directly onto the distal balloon of the delivery system and includes the ability to slide the sheath from covering the collapsed replacement valve so that the balloon can thereafter be expanded for permanently deforming and expanding the metal structure of the replacement valve into a permanent position at the pulmonary valve annulus.

Percutaneous aortic valve replacement procedures are also being investigated. One such valve that has been successfully deployed from a catheter delivery system is the CoreValve aortic valve and system, that is also available from Medtronic, Inc. The CoreValve aortic valve replaces the aortic valve in patients with severe aortic stenosis. The valve leaflets are provided by utilizing a bovine pericardial valve that is sutured to the expandable metal frame. This expandable metal frame, however, utilizes Nitinol metal allow so that the frame and thus the aortic valve is self-expanding for controlled deployment at the aortic valve annulus. This frame structure is typically around 5 cm long and is shaped along its length with a non-uniform diameter for improved anchoring of the aortic valve in position at the valve annulus. Further disclosure of aspects of the CoreValve aortic valve and delivery system are provided within U.S. Pat. Nos. 7,682,390, 7,780,726 and 7,892,281.

Delivery of the CoreValve aortic valve prosthesis or any other percutaneous and self-expandable aortic valve prosthesis typically requires a movable sheath at the distal end of a delivery system that maintains a compressed valve prosthesis beneath the sheath. Retraction of the sheath in a proximal direction of the delivery system as controlled from the proximal end of the delivery system is controlled for deploying the self-expandable valve prosthesis from one end thereof to another. Specifically, a distally positioned end of the valve prosthesis initially expands as the sheath is retracted while a proximally positioned end of the valve prosthesis remains collapsed within the confines of the sheath. A gradual expansion is thus controlled so that the full prosthetic valve is deployed in position, such as at a particular valve annulus. Typically, controlled expansion is conducted by maintaining the prosthetic valve as positioned on the distal end of the delivery system at a precise position, such as determined by fluoroscopy, while sliding the sheath proximally relative to the prosthetic valve and distal end of the delivery system. Self-expansion of the valve prosthesis deploys the prosthesis in this precise position and expansion of the metal frame of the prosthetic valve anchors the prosthetic valve in place. The sliding movement of the sheath can be conducted manually by a surgeon, for example, and such movement can be facilitated and controlled by mechanical means incorporated within a handle at the proximal end of the delivery system.

One such delivery system that has been designed for delivery of a self-expanding valve prosthesis is the AccuTrak™ delivery system that is commercially available from Medtronic, Inc. and is provided as a part of a system including the CoreValve aortic valve prosthesis, discussed above.

SUMMARY

The present invention overcomes shortcomings and deficiencies of prior art delivery systems by providing a prosthetic valve delivery system that is improved in controllability by way of a proximal handle system. Such a handle system of the present invention advantageously permits a controlled fine or micro movement of a distal sheath for uncovering a prosthetic valve for deployment thereof, and also permits a quick-release for a gross or macro movement to the sheath. Also, a packaging tray of the present invention provides for effective protective packaging along with storage and shipping ability, and also advantageously provides for a preparation tray for a surgeon to use just prior to a surgical procedure.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
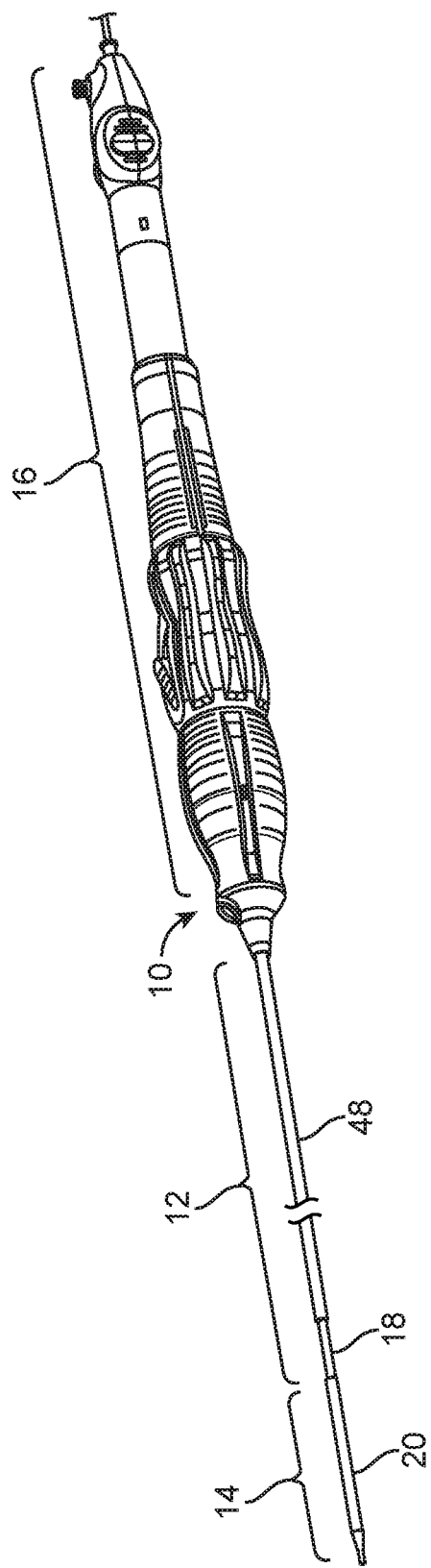
FIG. 1 is a perspective view of a delivery system in accordance with the present invention including a control handle assembly that is provided at a proximal end of the delivery system for selectively controlling movement of a prosthesis covering sheath at a distal end of the delivery system, which handle assembly controls both micro movement and a quick-release macro movement of the sheath, along with releasable components of the delivery system in order to facilitate quicker and easier delivery, system withdraw, and deployment of a prosthetic heart valve.

Referring now to the Figures, wherein the components are labelled with like numerals throughout the several Figures, and initially to FIG. 1, an exemplary delivery system 10 is illustrated for percutaneous insertion and implantation of a biological valvular replacement to a desired implant location, such as within a patient's heart. A prosthetic heart valve can be delivered by delivery systems of the present invention as such prosthetic heart valves can be designed for replacement of the aortic valve, mitral valve, tricuspid valve, or pulmonary valve by way of a patient's vasculature, such as including access through a patient's femoral artery or femoral vein, or otherwise, as appropriate in accordance with known or developed delivery techniques utilizing percutaneous delivery. Delivery systems according to the present invention improve the ease and accuracy of prosthetic valve delivery through the vasculature and avoid deployment difficulties related to the need to control the delivery and deployment actions at the distal end of such a delivery system from a proximally provided control handle.

Delivery system 10 is preferably used for delivering an expandable metal frame valve to a desired implant location, such as by way of, the femoral artery, the femoral vein, the pulmonary vein, a valved conduit, or otherwise. One preferably expandable valve that is desired to be delivered by the delivery system 10 of the present invention is the CoreValve aortic valve, as is commercially available from Medtronic, Inc., the assignee of the present invention, and as certain aspects thereof are described within U.S. Pat. Nos. 7,682,390, 7,780,726 and 7,892,281, the entire disclosures of which are incorporated herein by reference.

As shown in FIG. 1, delivery system 10 generally comprises a catheter portion 12, a distal deployment portion 14, and a proximal control handle portion 16 by which the deployment portion 14 is effectively controlled. The catheter portion 12 is preferably of a length and size so as to permit a controlled delivery of the deployment portion 14 to a desired implant location of a patient's heart, for example. Preferably, the catheter portion 12 includes features to enhance manoeuvrability, steerability and advancement of the deployment portion 14 to the point of implantation, as further discussed below. The deployment portion 14 provides the means by which a metal frame prosthetic valve can be mounted for delivery to the implantation location and further provides for allowing the expansion of the metal frame prosthetic valve for effective deployment thereof. The control handle portion 16 preferably controls movements as translated to the deployment portion 14 by way of elongate structure of the catheter portion 12. Controlled functionality from the control handle portion 16 is preferably provided in order to permit expansion and deployment of a metal frame prosthetic valve at a desired location, such as a heart valve annulus, and to provide for ease in the delivery and withdrawal of the delivery system through a patient's vasculature.

The catheter portion 12 comprises plural elongate elements preferably including a flexible outer shaft 18 that is operatively connected with the control handle portion 16 so as to be movable by operation of the handle control portion, as described below, and that is connected with a sheath 20. Movement of the sheath 20 proximally from its distalmost position exposes a plunger 22 that is connected with an inner shaft 24. The inner shaft 24 is also operatively connected with the control handle portion 16, but so as to be relatively fixed with respect to the outer shaft 18 and sheath 20. That way, relative movement of the outer shaft 18 and sheath 20 with respect to the plunger 22 and inner shaft 24 provides for a controlled covering or exposing of the plunger 22. More particularly, when an expandable prosthetic heart valve is collapsed onto the plunger 22, withdrawing of the sheath 20 to expose the prosthetic valve as collapsed onto the plunger 22 provides for controlled expansion of the prosthetic valve and controlled deployment thereof. Where the prosthetic valve comprises a metal frame valve that is self expanding, the proximal movement of the sheath 20 allows the metal frame of the valve to expand for deployment of its valve leaflets in position as located by delivery system 10.

Figure 4:
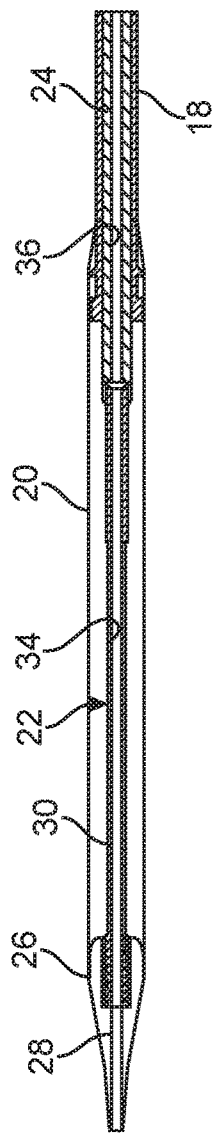
FIG. 4 is an enlarged cross-sectional view of the plunger and sheath portion of the delivery system of the delivery system of FIG. 3.
Figure 5:
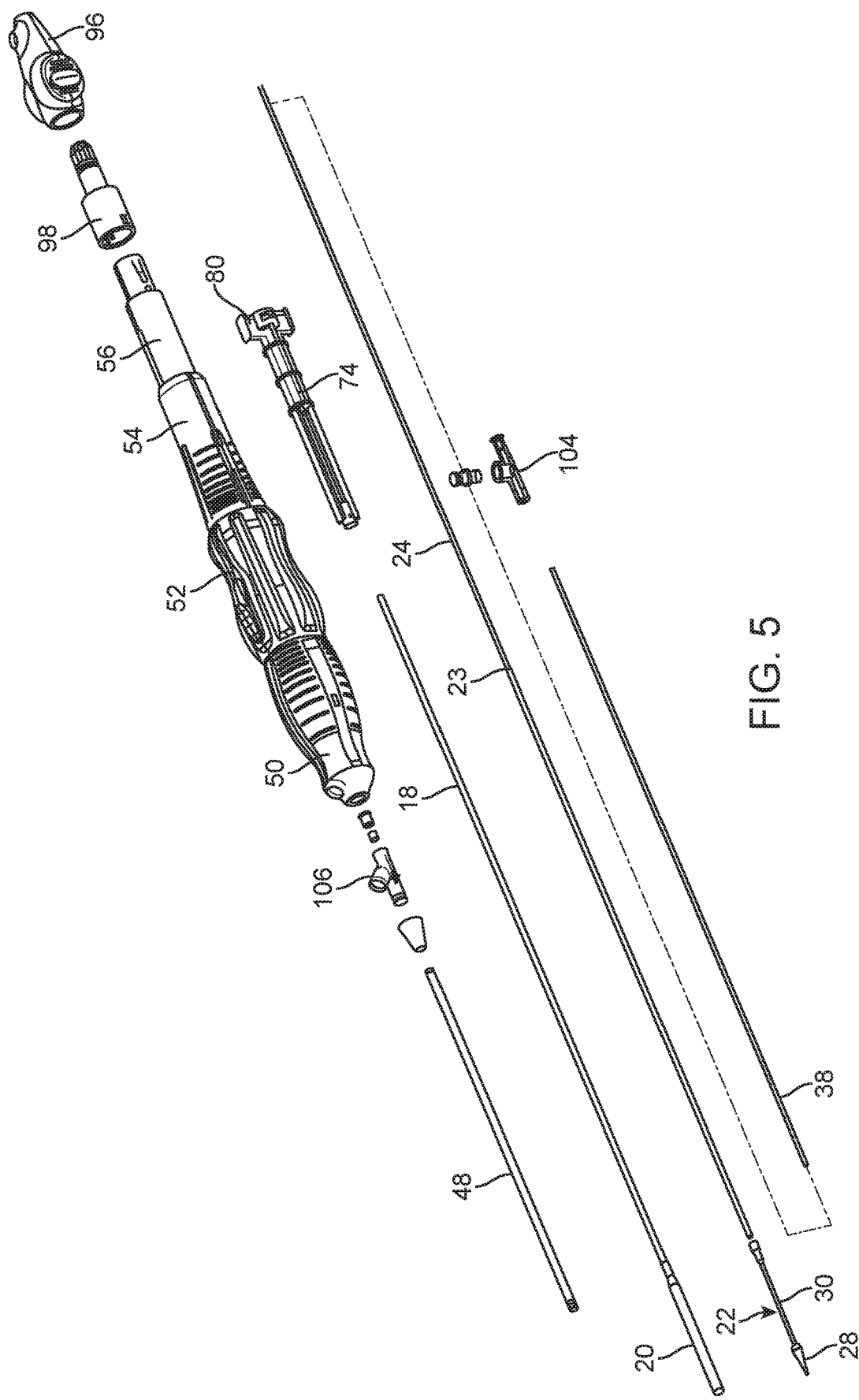
FIG. 5 is a partially exploded view of the delivery system of FIGS. 1-4 illustrating the manner of assembly of an inner shaft relative to an outer shaft and with respect to a stabilizing shaft and a flush tube.

With reference to FIG. 4, in particular, the sheath 20 is illustrated at a distalmost or closed position with a leading edge thereof abutting against a perimetric shoulder 26 of a nosecone 28 that is provided as the leading feature of the plunger 22. Proximally from the nosecone 28, the plunger 22 comprises a reduced diameter portion 30 onto which an expandable prosthetic heart valve is to be collapsed. At the proximal-most end of the plunger 22, a increased diameter portion 32 defines a proximal edge for positioning the collapsed valve distally and also provides a connection point for connecting the plunger 22 to the distal end of the inner shaft 24. A lumen 34 passing axially through the plunger 22 also preferably aligns with a lumen 36 of the inner shaft 24 as these components are fixed together to provide a continuous lumen.

A flush tube 38 is provided that preferably extends within the inner shaft 24 passing through the lumen 36. Fluid communication and transport is provided by appropriate passage throughout the system. Orifices are also provided, as needed, for fluid to pass out of the delivery system for flushing or other purposes. The flush tube 38 also preferably includes an axial lumen extending entirely though it, the purpose of which is for receiving a guide wire, as well known, in order for the delivery system 10 to be guided along a patient's vasculature to an implant location. The guide wire, not shown, may be, for example, a 0.089 cm extra stiff guidewire as manufactured by Amplatzer of Golden Valley, Minn., and be used in a conventional manner to guide the delivery system along it and with its distal end guided to its desired implant location.

Figure 2:
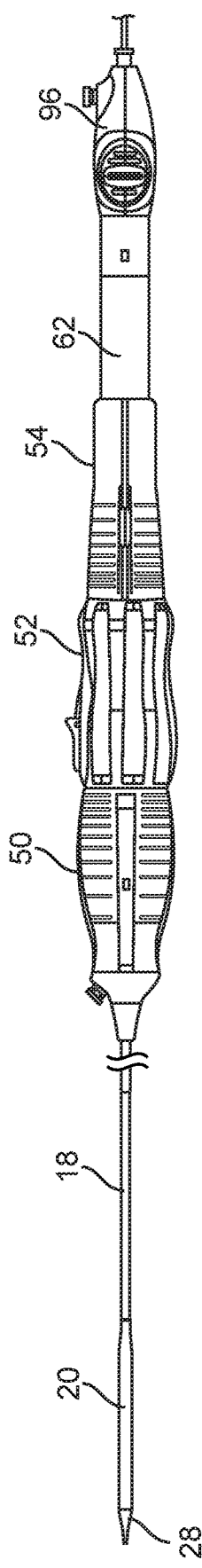
FIG. 2 is a side view of the delivery system of FIG. 1 illustrating a front grip portion, a translating rotator portion including a quick-release button, a proximal hand rest portion, and a tip retractor portion.
Figure 3:
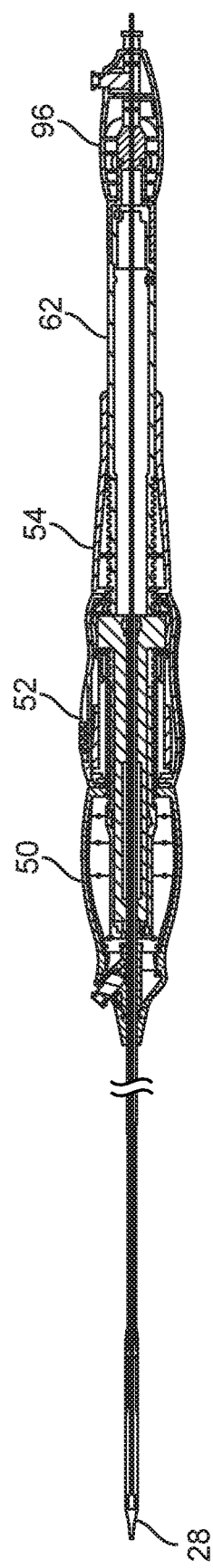
FIG. 3 is a cross-sectional view of the delivery system of FIG. 2 illustrating an internal screw shaft that is fixed with a plunger at a distal end of the delivery system by an inner tube and that is relatively movable to an outer tube that is connected with a sheath at the distal end of the delivery system so that the translating rotator moves along the internal screw shaft to move the sheath relative to the plunger as the plunger is maintained at a desired deployment position.

The catheter portion 12 of the delivery system 10 also preferably comprises a stability shaft 48 that is also operatively connected with a distal end of the control handle portion 16 and that surrounds the outer shaft 18 over at least a part of its length. Preferably, the stability shaft comprises a braided stainless steel inner layer with a flexible plastic outer layer. Such a stability layer facilitates the advancement and steering of the delivery system along a guide wire and through a patient's vasculature by improving the pushability of the delivery system 10, improving torque transmission to the tip of the delivery system 10 for steerability, and by preventing kinking along the catheter portion 12 of the delivery system The control handle portion 16 is designed, among other things, for controlling the covering and the withdrawal of the sheath 20 with respect to the plunger 22, and further with respect to an expandable prosthetic heart valve as such can be collapsed onto the plunger 22, as described above. With reference to FIGS. 2 and 3, in particular, the control handle portion 16 comprises a front grip 50, a micro-control actuator 52, and a carriage 54 as those elements that are grasped and manipulated by a surgeon during a procedure according to the present invention for controlling the covering and withdrawing of the sheath 20 relative to the plunger 22. This functionality is achieved by a relative movement between the front grip 50 and the micro-control actuator 52, as the micro-control actuator 52 is operatively connected with the outer shaft 18. Specifically, the micro-control actuator 52 and the carriage 54 can translate together along a screw shaft 56 that is fixed with the front grip 50.

Figure 6:
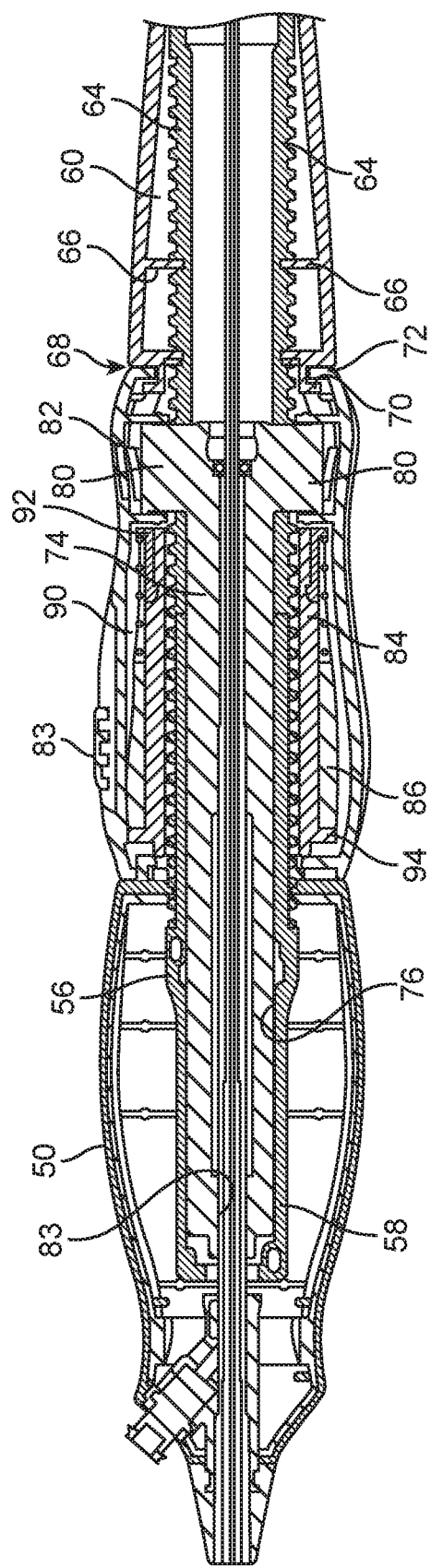
FIG. 6 is an enlarged cross-sectional view of an assembly including the internal screw shaft along with a drive tube that is internal to the screw shaft, as such assembly is positioned within the front grip, translating rotor and proximal hand rest.
Figure 7:
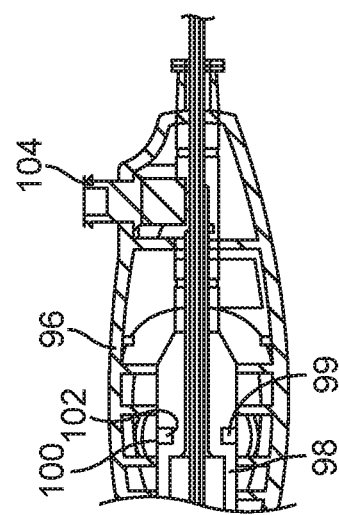
FIG. 7 is an enlarged cross-section of a quickly releasable tip retractor.

As shown in FIG. 6, the screw shaft 56 includes a distal portion 58 that fits within and is fixed to the front grip 50. More proximally, the screw shaft increases in diameter to an elongate threaded portion 60 that extends at least through the axial distance of the micro-control actuator 52. Proximally of the threaded portion 60, a non-threaded portion 62 extends along which the carriage 54 can translate. The micro-control actuator 52 preferably translates along the screw shaft 56 by rotation thereof in the manner of a nut moving along a threaded shaft. The carriage 54 is preferably axially movable along the screw shaft 56 without rotating as the carriage 54 is driven by the micro-control actuator 52. As illustrated, the screw shaft 56 includes a pair of diametrically opposed slots 64 that extend over a proximal portion of the threaded portion 60 of the screw shaft. Pins 66 are provided inward from the carriage 54 and to extend into the slots 64. This arrangement allows the carriage 54 to translate along the screw shaft 56 without rotating. The carriage 54 is also preferably axially connected to the micro-control actuator 52 such as shown at 68, whereby an inner annular flange 70 of the carriage 56 fits within an outer annular flange 72 of the micro-control actuator 52. This arrangement allows the micro-control actuator 52 to rotate relative to the carriage 56, but to be axially movable together.

In order to functionally connect the outer shaft 18 so as to translate with the micro-control actuator 52, a T-shaft 74 is movably provided within an internal axial passage 76 of the screw shaft 56. The slots 64 also are open into the internal axial passage 76. The T-shaft 74 comprises a rod portion 78 and a pair of tabs 80 that are provided to extent through the slots 64 of the screw shaft 56 and to fit within an annular recess 82 of the internal side of the micro-control actuator 52. Preferably, the tabs 80 fit closely within the annular recess 82 so that there is a direct movement of the T-shaft 74 in the axial direction as the micro-control actuator 52 moves axially along the screw shaft 56 when rotated. This length of the slots 64 define the range of travel of the T-shaft 74 and thus the micro-control actuator 52 along the screw shaft 56. The rotation is not transmitted to the T-shaft 74 as the interaction of the tabs 80 and slots 64 prevent rotation of the T-shaft relative to the screw shaft 56.

The T-shaft is also operatively fixed with the outer shaft 18 for moving the outer shaft and thus the sheath 20 under the control of the micro-control actuator 52. The proximal end of the outer shaft 16 is preferably provided to extend within a lumen 83 of the T-shaft. The outer tube and be bonded to the lumen 83 of the T-shaft anywhere along contacting surfaces of the length of contact as desired. As a result of this arrangement, axial movement of the T-shaft 56 as controlled by the micro-control actuator 52 is directly translated to the outer shaft 18 and thus the sheath 20.

Figure 8:
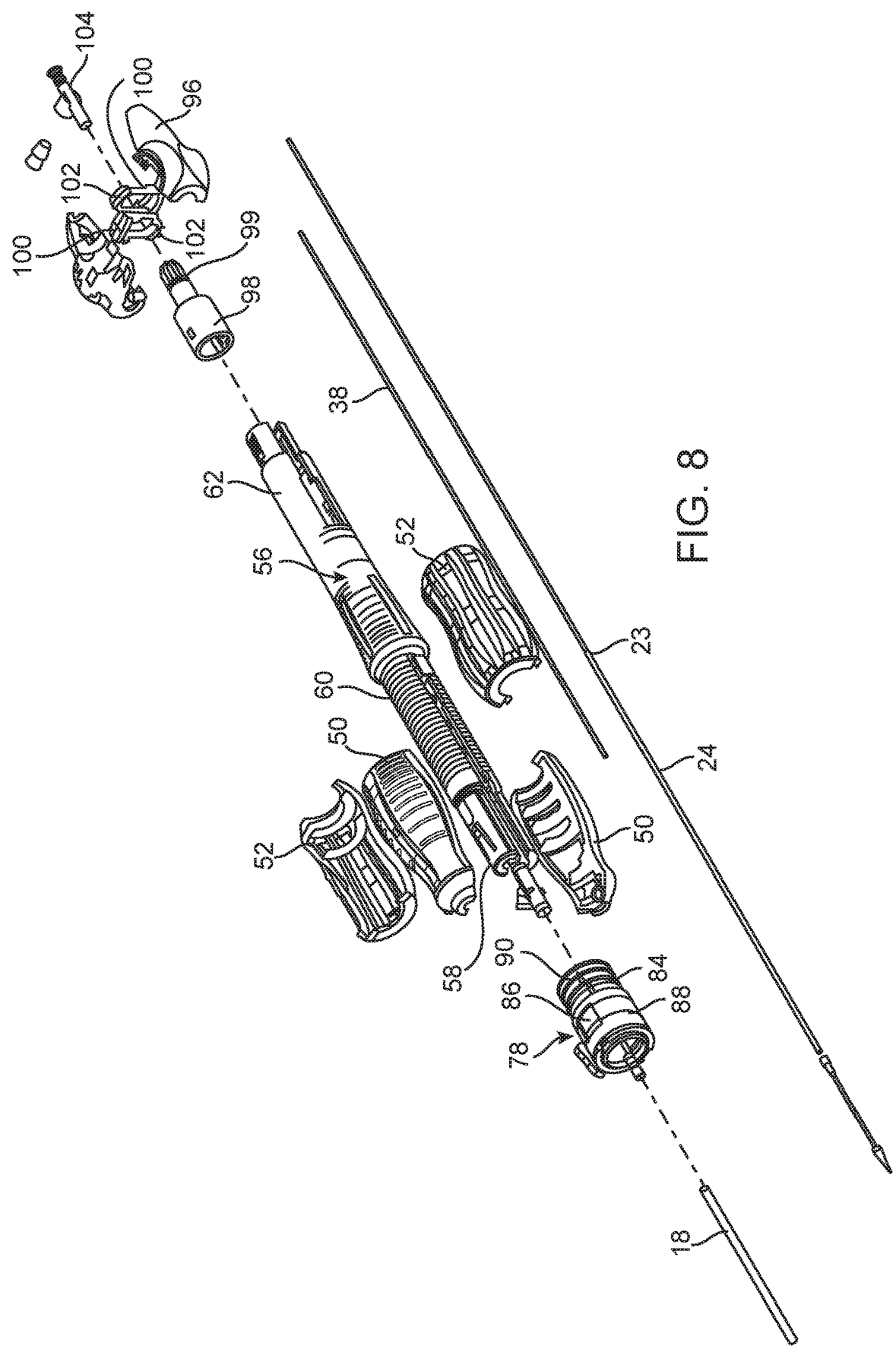
FIG. 8 is a partially exploded view of the delivery system of the previous figures showing the control handle assembly components.
Figure 10:
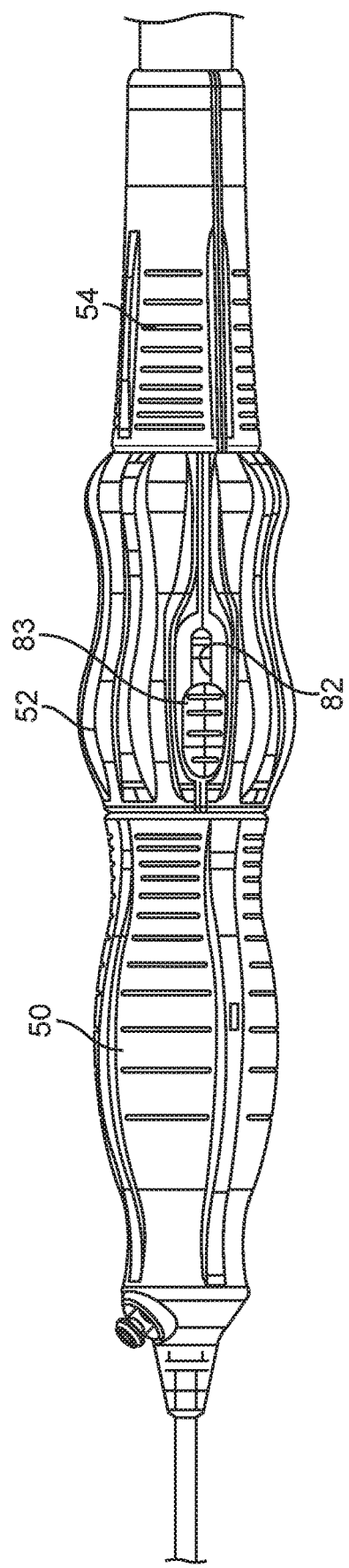
FIG. 10 is a top view of the handle assembly with the quick-release button shown in a locked position along a slide.

In accordance with another aspect of the present invention, the control handle portion 16 includes a macro-actuation ability. Between the micro-control actuator 52 and the screw shaft 56, a threaded insert assembly 78 is provided, as shown in FIGS. 6 and 8, that functions to releasably engage with the threaded portion 60 of the screw shaft 56. Female threads of the insert assembly 78 releasably engage with the male threads of the treaded portion 60 so that when they are engaged, rotation of the the micro-control actuator 52 causes translation of the micro-control actuator 52 along the screw shaft 56. When released, the micro-control actuator 52 is permitted to freely slide along the screw shaft 56 without rotation along a range of movement that is preferably sufficient to completely cover or uncover the valve support reduced diameter portion 30 of the plunger 22 by the sheath 20. This selective release is preferably controlled by sliding a release trigger 80, as shown also in FIG. 10, that is movable along a slot 82 of the micro-control actuator 52.

The threaded insert assembly 78, as illustrated, comprises an inner sleeve 84 that rides along the threaded portion 60 of the screw shaft 56 and that includes a pair of diametrically opposed flexible tabs 86 that are each provided with a threaded surface to engage with the threads of the threaded portion 60 when urged toward the screw shaft 56. The remainder of the inside surface of the inner sleeve 84 is non-threaded to simply slide along the threaded portion 60. The tabs 86 can be formed with the inner sleeve 84 and can be hingedly connected so as to be biased radially outward or away from the threaded portion 60. When the tabs 86 are permitted to move freely, the tabs 86 do not threadingly engage with the threaded portion 60, as they are biased outwardly, so that the sleeve 84, and thus the threaded insert assembly 78 can freely move along the screw shaft 56, as described above.

In order to engage the threads of the tabs 86 with the threaded portion 60 and to engage the micro-control actuator 52 for micro-control of the sheath 20, an outer sleeve 88 can be provided, as illustrated, that slides along an outer surface of the inner sleeve 84. A compression spring 90 is also preferably provided along the outer surface of the inner sleeve 84, and is illustrated to bias the outer sleeve 88 distally. Spring 90 is shown as engaged with a proximal end of the outer sleeve 88 and with an annular flange 92 that is provided at a proximal end of the inner sleeve 84. A distal annular flange 94 of the inner sleeve provides a stop for movement of the outer sleeve 88 distally. As such, the outer sleeve 88 of this preferred embodiment of a quick release assembly to permit macro-control can move along the surface of the inner sleeve 84 under the distal bias of the spring 90. In the distal-most position of the outer sleeve 88, the tabs 86 are forced against their outward bias to be positioned radially inwardly and with the female threads of the tabs 86 engaged with the male threads of the threaded portion 60 of the screw shaft 56. That is, with the outer sleeve 88 in its distal-most position, the micro-control actuator 52 is effectively engaged for micro-control of movement of the sheath 20.

The outer sleeve 88 is preferably connected with the release trigger 80 so as to be movable with the trigger 80 along the range of movement that is permitted by the length of the slot 82. That way, sliding the trigger 80 proximally against the bias of the spring 90 moves the outer sleeve 88 proximally. After sufficient movement of the outer sleeve 88, the tabs 86 are released from engagement with the inner surface of the outer sleeve 88 and the tabs 86 move radially outward with their threads moved out of engagement with the threaded portion 60 of the screw shaft 56. Macro-adjustment of the sheath 20 is thus possible with the trigger moved sufficiently proximally. Release of the trigger 80 allows spring 90 to move the outer sleeve 88 distally, which action forces the tabs 86 radially inwardly into engagement with the threaded portion 60 of the screw shaft 56 and activates the micro-control of the sheath 20 by the micro-control actuator 52.

At the proximal end of the delivery system 10, a tip retractor 96 is provided that is releasably connected with the delivery system 10. Preferably, the tip retractor 96 is attached to the proximal end of the inner shaft 24 so that when the tip retractor 96 is disconnected from the delivery system 10, as described below, the inner shaft 24 and the plunger 22 can be pulled proximally up to the point of engagement between the shoulder 26 of the nosecone 28 and the leading edge of the sheath 20. As will be more apparent with the operational description below, the greatest degree of proximal movement of the nosecone 28 to the leading edge of the sheath 20 as a result of disconnecting the tip retractor 96 will be when the micro-control actuator 52 is translated to its proximal-most position. Once the micro-control actuator 52 is rotated so that the micro-control actuator 52 is fully proximally moved, the sheath 20 assumes its fully withdrawn position relative to the plunger 22, and to a prosthetic heart valve device when supported thereon. If at this point, the trigger 80 is moved proximally, the micro-control actuator 52 can be quickly slid along the screw shaft 56 to its distal-most position and the sheath 20 will be moved distally fully forward to cover the plunger and engage the nosecone 28. However, if the micro-control actuator 52 is left at the proximal-most position, or at any position that is proximal from the distal-most position of the micro-control actuator 52, the tip retractor 96 can be disconnected from the delivery system and the plunger pulled proximally by way of the inner shaft 24 until the nosecone 28 abuts with the leading edge of the sheath 20.

In order to provide the quick disconnect between the tip retractor 96 and the remainder of the delivery system 10, an adapter 98 is provided that is connected to prevent axial movement or rotation to the proximal end of portion 62 of the screw shaft 56. The adapter 96 is preferably reduced in diameter to fit within a passage of the tip retractor and includes an annular recess 99. Spring loaded push buttons 100 are also preferably slidably supported along openings of the tip retractor 96 and biased with engagement portions 102 thereof fitted into the annular recess 99. That way, pushing both the buttons 100 inward causes a release of each of the engagement elements thereof from the annular recess 99 and thus a disconnection of the tip retractor 96 from the adapter 98, in particular, of the delivery system 10.

Also preferably incorporated within the tip retractor 96 is a flush tube hub 104 so that the flush tube 38 can pass through the delivery system proximally. The flush tube hub 104 also provides for the ability to provide fluids throughout and from the delivery system as needed.

Figure 9:
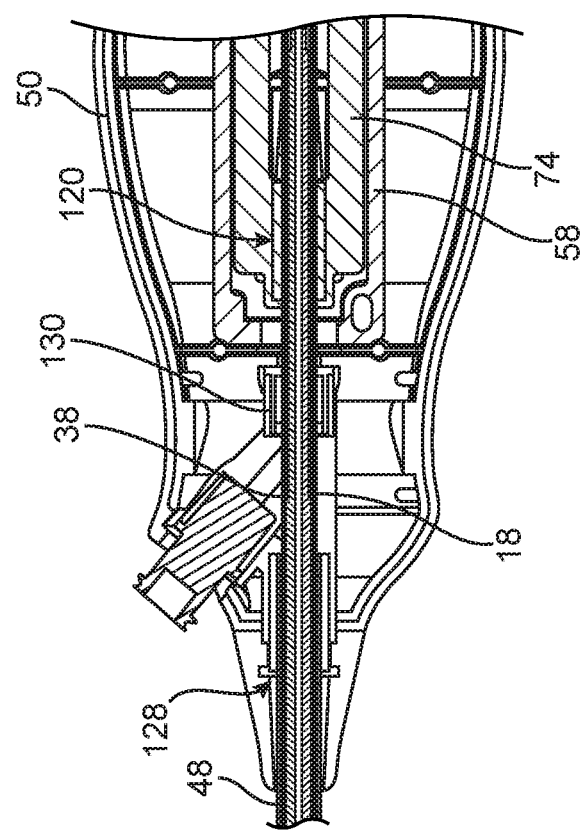
FIG. 9 is an enlarged cross-sectional view of a distal portion of the handle assembly including a portion of the front grip and of the internal screw shaft.

Additionally, a flush port 106 is preferably provided at the distal end of the front grip 50 with reference to FIG. 9. An access passage 108 of a hub 110 at the distal end of the front grip 50 provides for fluid flow from the flush port. FIG. 9 also illustrates the preferred provision of a strain relief element 110 and a manner of connection of the stability shaft 48 to the hub 110 at the distal end of the front grip 50. Insertion of the stability shaft 48 partially into the hub 110 positions the end of the stability shaft 48, and a bond is preferably made between the stability shaft 48 and the hub 110.

Another aspect of the present invention resides within the shaping, sizing and positioning of the control handle portion 16 of the delivery system 10. Specifically, the front grip 50, micro-control actuator 52, and carriage 54 are positioned in that order going proximally from the distal end of the front grip so that when the micro-control actuator 52 is fully distally positioned, and as the carriage 54 is positioned axially adjacent to the micro-control actuator 52 by it axial connection thereto, a smooth contoured outer surface profile is created along with the front grip 50. In use, as described more below, the control handle portion 16 is typically gripped at the front grip 50 by the left hand (assuming a right handed surgeon). The surgeon's right hand is then easily positionable partially on the carriage 64 and partially on the micro-control actuator 52. The right palm would rest on the contoured surface of the carriage 54 while the right fingers could be positioned for manipulation of the micro-control actuator 52. The right thumb and first couple fingers can grasp and rotate the micro-control actuator 52 from this position, and the right thumb is positioned for easy sliding of the trigger 80 when desired.

Preferably, the front grip 50 is contoured with a curved outer surface creating an outward bulge to facilitate the surgeon's hand similar to a bicycle grip. The Carriage 54 is preferably sloped away from the micro-control actuator 52 to provide a palm rest. The micro-control actuator 52 is preferably contoured with an inward curve between outer curves, each of which outer curves tend to curve back to the level of the surface of the adjacent surfaces of the front grip 50 and the carriage 54, respectively. The inward curve provides a gripping zone for the surgeon's thumb and forefinger to affect easy rotation of the micro-control actuator 52. Overall, the profile from the leading or distal end of the control handle portion 16 to the trailing or proximal end of the control handle portion 16 is preferably a series of smooth contours including curves that facilitate easy gripping and manipulation of the control handle features, as discussed above.

An additional aspect of the present invention relates to a manner of packaging a delivery system 10 of the present invention for ease in providing all the necessary elements of the delivery system 10 to allow for storage until needed, and to facilitate quick and easy removal and set up of the delivery system with a prosthetic heart valve for use in a surgery by a surgeon at the time of the operation.

Figure 11:
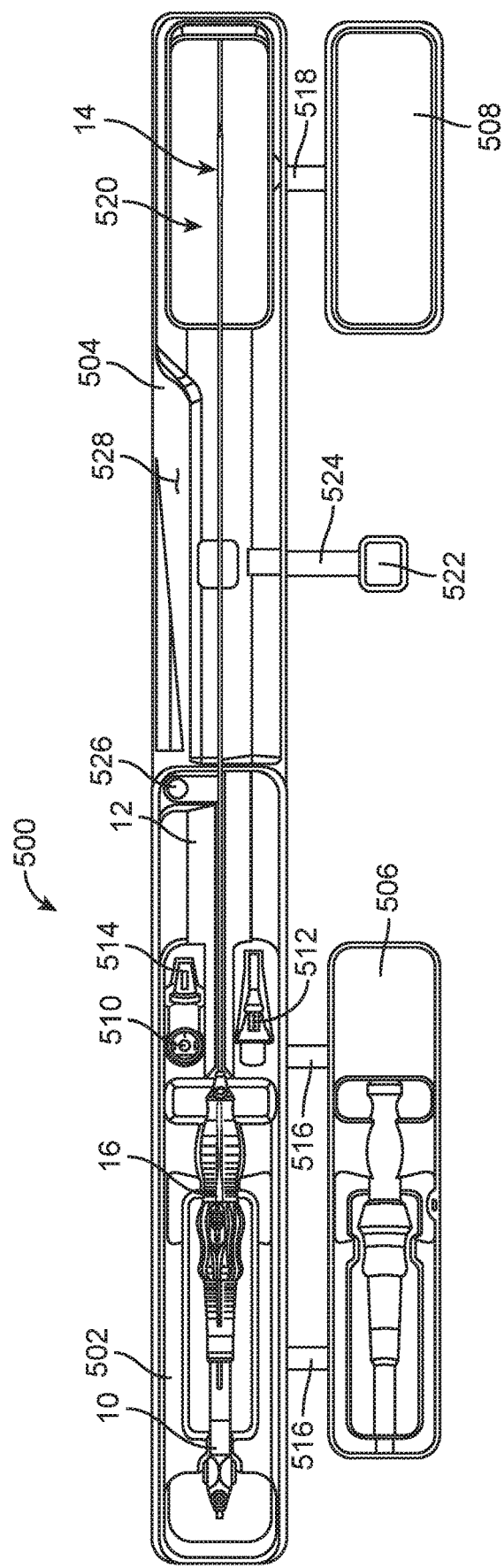
FIG. 11 is top view of a packaging and preparation tray in accordance with another aspect of the present invention including a proximal portion and a pivotal distal portion, the tray being illustrated with proximal and distal securing portions to the side of the main tray assembly and with a delivery system in accordance with the present invention also positioned within the main tray assembly.

A packaging and preparation tray assembly 500 is illustrated in FIG. 11. The packaging and preparation tray assembly 500, as illustrated, comprises a first main tray 502 for supporting a proximal portion of a delivery system 10 in accordance with the present invention and a pivotal second main tray 504 for supporting a distal portion of such a delivery system 10. The tray assembly 500 is illustrated as also including first and second securing trays 506 and 508 that are shown as positioned to the side of the first and second main trays of the tray assembly 500 and with a delivery system 10 in accordance with the present invention also positioned within the tray assembly 500.

The first main tray 502 preferably is formed to provide supporting features that are based upon the shape and dimensions of a delivery system 10 of the present invention. Preferably, the first main tray 502 is formed to support about half the length of the delivery system 10, such as including the handle control portion 16 and a part of the catheter portion 12, as such portions are described above. The second main tray 504 also preferably supports about half of the delivery system 10, such as including part of the catheter portion 12, and the deployment portion 14, as such terms are also described above.

The first and second main trays 502 and 504 are preferably formed with supports that are shaped to correspond with portions of the delivery system 10 along its length so as to keep the delivery system 10 in place as packaged. Such formed support structures are well known within plastic molding and forming technologies for packaging. As illustrated, the first main tray 502 can also include similarly formed support shapes for a prosthetic heart valve 510, such as conventionally provided within a sealed container, and a loading funnel 512 and adapter 514, as are used in the loading process of the valve 510 onto the delivery system 10, as discussed further below. The second main tray 504 is illustrated as formed to facilitate the elongate catheter portion 12 and deployment portion 14 as extended linearly from the first main tray 502. That is, the catheter portion 12 and thus the delivery system 10 can be linearly arranged without bending as packaged within the tray assembly 500 by having the first and second main trays 502 and 504 arranged end to end.

Figure 12:
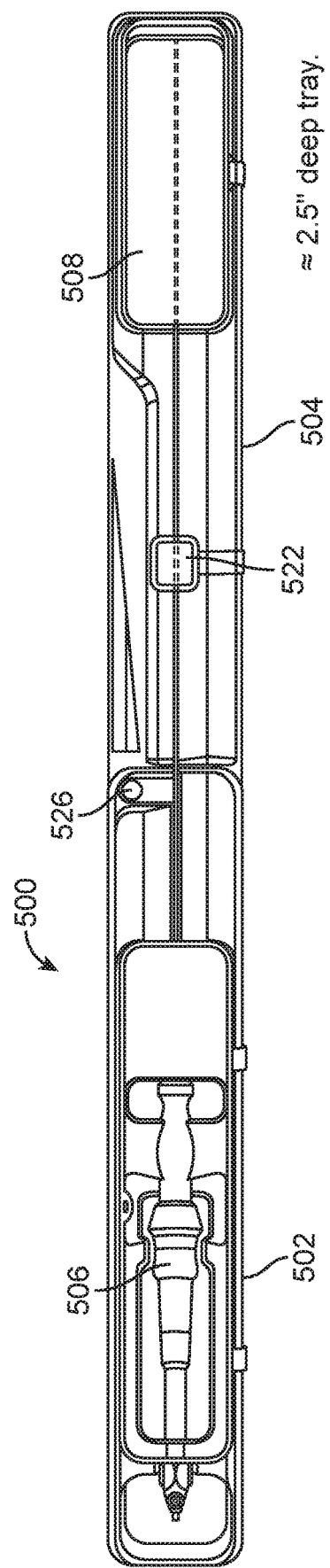
FIG. 12 is a top view similar to FIG. 11, but with the proximal and distal securing portions positioned over portions of the main tray assembly and holding a delivery system in accordance with the present invention in place.

FIG. 11 shows the tray assembly 500 with securing trays 506 and 508 not positioned over and covering portions of the delivery system 10, as such is illustrated in covered positions in FIG. 12. Securing tray 506 is shown attached to first main tray 502 by a pair of flexible hinge straps 516. These straps 516 allow the securing tray 506 to be folded over the first main tray 502 so that the securing tray 506, which is sized and formed to also fit with components of the delivery system 10, can secure the delivery system handle portion 16 with the tray assembly 500. Likewise, the securing tray 508 is movable to the second main tray 504 by one or more straps 518 (one shown) so that the securing tray can be folded over and fit against a part of the second main tray 504 for holding part of the catheter portion 12 and deployment portion 14 of the delivery system 10 in place within the tray assembly 500. Preferably, each of the securing trays 506 and 508 include edges that are sized to be tightly fitted within edges of the first and second main trays 502 and 504, respectively, as known, in order for the securing trays 506 and 508 to maintain their respective securing positions to the first and second main trays 502 and 504. Such fitting can include a snap-type fit, as known, for connected of the two, or the corresponding edges can be heat sealed, bonded, or otherwise connected to create a packaged delivery system.

With respect to the securing tray 508, in particular, a further functionality is preferably provided. That is, the securing tray 508 also can be used to effectively close a saline bath area 520 that is preferably formed into the second main tray 504 along the portion thereof that is designed to support the deployment portion 14 of the delivery system 10, at least. The bath area 520 can be formed in the second main tray 504 and can be filled with cold saline solution, as such solutions are well known for this purpose, which solution is used during a loading process of a tissue heart valve. The second main tray 504 is also shown with a snap-fit holding element 522 that, like the securing trays 506 and 508 is attached by a strap 524 so that the holding element 522 can be folded over the second main tray 504 for securing a portion of the catheter portion 12 of the delivery system 10 in place. This feature is of particular advantage during a tissue valve loading process, as described below, for holding the catheter portion 12 in place while collapsing a metal frame tissue valve onto the plunger 22 of the deployment portion 14 of a delivery system 10 in accordance with the present invention.

FIG. 12 illustrates that first and second main trays 502 and 504 are each of an elongate shape themselves and can be arranged end-to-end with each of the securing trays 506 and 508 positioned over and preferably snap-fit in place along with the holding feature 522. This is a preferable storage and/or shipping configuration of the tray assembly 500 of the present invention. By loading the delivery system 10 into the tray assembly in this configuration, bending of the catheter portion 12 is avoided. Conventional packages for such elongate catheter devices bend the catheter portions thereof in a U-shape, which can cause a set of a curve within the catheter tubing over time. The configuration above avoids any such concern.

Figure 13:
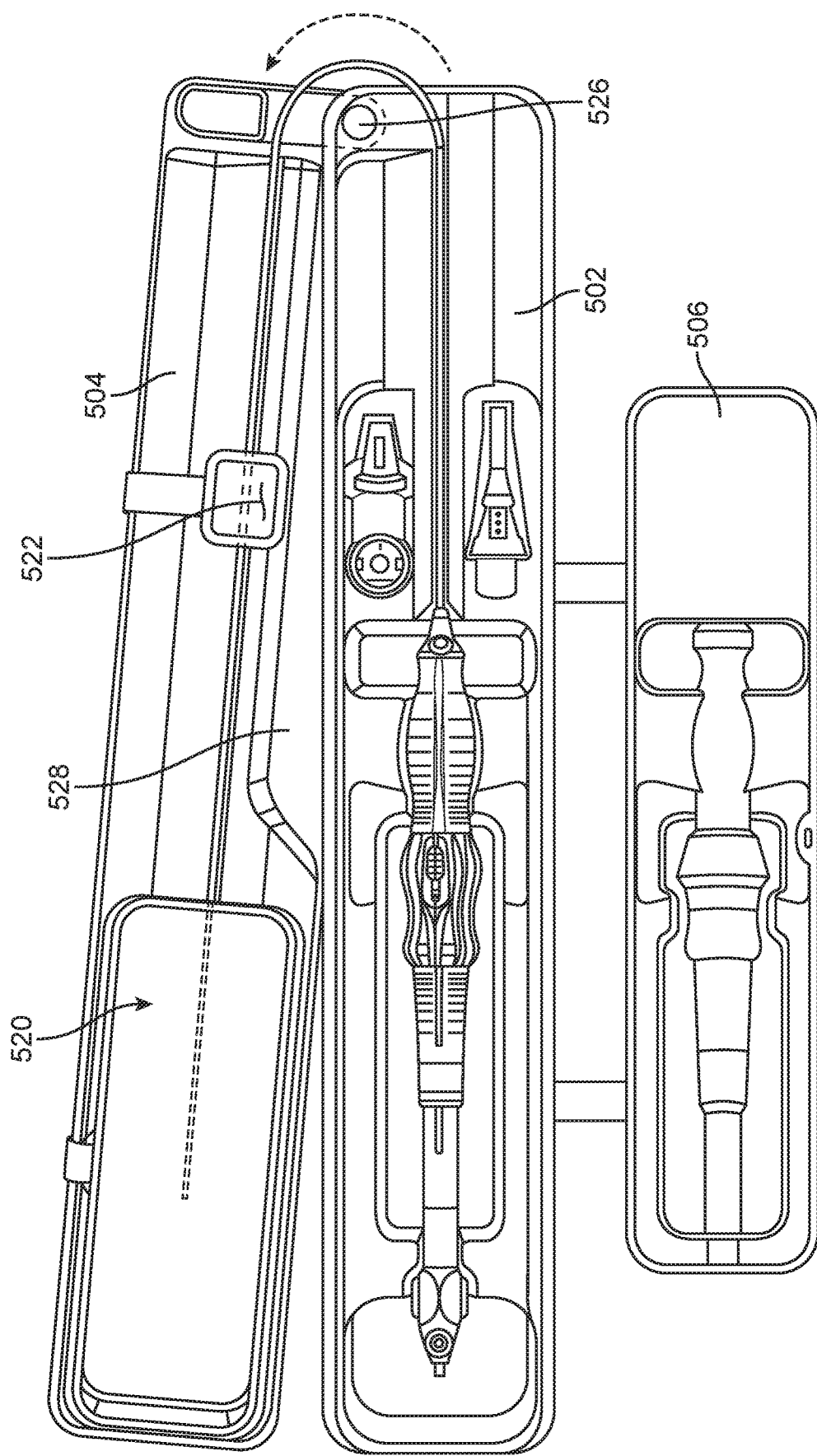
FIG. 13 is a top view of the packaging and preparation tray of FIGS. 11 and 12 but with the distal portion thereof pivoted to a position adjacent to the proximal tray portion, which position is configured to allow preparation, such as on a sterile table surface, of the delivery system and loading a prosthetic heart valve device on the distal end of the delivery system within a controlled environment, such as temperature controlled saline.
Figure 14:
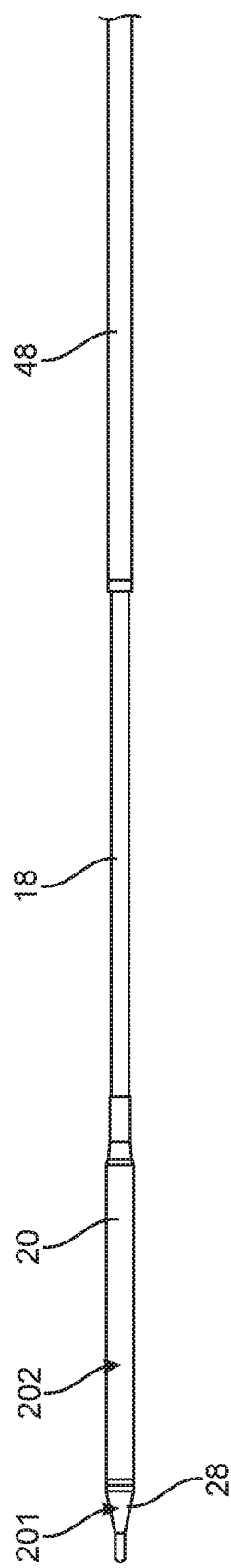
FIG. 14 is a schematic view of another aspect of the present invention including the provision of specifically coated portions of a delivery system to improve the insertion and withdrawal of the delivery system within the vasculature of a patient and for controlled deployment of a heart valve prosthesis.

The first and second main trays 502 and 504 are also preferably operatively connected together so that they can be arranged end-to-end, as shown in FIGS. 11 and 12, and side-to-side, as illustrated in FIG. 13. To do this, a hinge 526 can be provided, as shown, that includes a pintle and bearing surface arrangement, as such can be formed into the respective corners of the first and second main trays 502 and 504. Preferably, the corresponding formed elements of such a hinge are snap-fit to keep the hinge from coming apart. To facilitate rotational movement around the hinge 526, the second main tray 504 is provided with a thin portion 528 that easily slides beneath the corner of the first main tray 502 so that a substantial side-by-side arrangement of the first and second main trays 502 and 504 can be configured by simply rotating the second main tray 504 about the hinge 526 while the first main tray 502 is stationary. Of course, either or both trays can just as easily be rotated to one another.

FIG. 13 illustrates the tray assembly in the rotated side-by-side configuration. Thin portion 528 of second main tray 504 is beneath a portion of the first main tray 502. In this configuration, the catheter portion 12 of a delivery system that is packaged within the tray assembly 500 is bent in a substantial U-shape. Moreover, the bath area 520 of the second main tray 504 is now located substantially adjacent to the proximal handle portion 16 of the delivery system. This position is advantageous for loading a tissue valve to the deployment portion 14 of the delivery system in that the elements of the handle control portion 16, as described above, can easily be manipulated while the tissue valve is prepared and loaded to the nearby deployment portion. In this regard, both micro-actuation and macro-actuation control of the sheath 20 at the distal end of such a delivery system 10 can be effected during the loading process.

By this packaging tray assembly, a first configuration is provided where the delivery system can be supported by the first and second main trays with the elongate catheter of the delivery system arranged to extend linearly from the first main tray to the second main tray. The packaging tray assembly also provides for a second configuration where the delivery system can be supported by the first and second main trays with the elongate catheter of the delivery system turned back in a U-shaped manner with the deployment portion of the delivery system positioned to the side of the control handle portion of the delivery system.

Another aspect of the present invention relates to the selective surface modification of surface of a delivery system according to the present invention. It is a purpose of the utilization of such selective surface modifications to improve the force that is necessary for insertion into and through an introducer, for example, (need more info here) and to reduce tracking forces throughout a patient's vasculature, including in particular, the aortic arch for a femoral artery approach to a patient's aorta.

Preferably surface modification of select delivery system surfaces comprises the coating of such select surfaces. Other surface modifying techniques are contemplated as well that may include treatments by certain types of energy, chemical non-coating treatments, mechanical treatments, such as surface polishing, and the like. It is also contemplated to perform multiple coatings or other techniques together to one surface or selectively to distinct surfaces as effective.

In accordance with the present invention, it has been found to improve functionality of loading of a prosthetic aortic valve, for example, onto the deployment portion 14 of a delivery system 10, as illustrated in Fig. In this regard, it is preferable to coat the delivery system nosecone 28 and the sheath 20 of a delivery system 10 with a hydrophilic coating. This portion of the delivery system does not need to be contacted during the valve loading process, as described above.

The invention claimed is:

1. A prosthetic heart valve delivery system comprising:
   an elongate catheter comprising a sheath and a shaft, at least a portion of the shaft residing within a lumen of the sheath, the shaft having a nosecone attached to a distal end thereof, the sheath configured to cover and uncover a collapsed prosthetic heart valve supported by the shaft;
   a handle comprising a sheath actuator operatively coupled to the sheath; and
   a shaft retractor releasably coupled to a proximal end of the handle and fixedly coupled to the shaft,
   wherein the sheath actuator is configured to provide a controlled translation of the sheath relative to the shaft when the shaft retractor is coupled to the handle, and
   wherein the shaft retractor is configured to translate the shaft relative to the sheath when the shaft retractor is released from the handle.

2. The delivery system of claim 1, wherein the sheath actuator is configured to be rotated to provide the controlled translation of the sheath relative to the shaft when the shaft retractor is coupled to the handle.

3. The delivery system of claim 1, wherein the shaft retractor includes push buttons to release the shaft retractor from the handle.

4. The delivery system of claim 3, wherein the push buttons comprise a pair of push buttons that are configured to be pressed radially inward to release the shaft retractor from the handle.

5. The delivery system of claim 1, further comprising a stability shaft surrounding the sheath.

6. A prosthetic heart valve delivery system comprising:
   an elongate catheter comprising an outer shaft and an inner shaft, at least a portion of the inner shaft residing within a lumen of the outer shaft, the inner shaft being attached to a nose cone at a distal end of the inner shaft;
   a handle comprising an actuator operatively coupled to the outer shaft; and
   a tip retractor releasably coupled to a proximal end of the handle and fixedly coupled to the inner shaft,
   wherein the actuator is configured to provide a controlled translation of the outer shaft relative to the inner shaft when the tip retractor is coupled to the handle, and
   wherein the tip retractor is configured to translate the inner shaft relative to the outer shaft when the tip retractor is released from the handle.

7. The delivery system of claim 6, wherein the actuator is configured to be rotated to provide the controlled translation of the outer shaft relative to the inner shaft when the tip retractor is coupled to the handle.

8. The delivery system of claim 6, wherein the tip retractor includes push buttons to release the tip retractor from the handle.

9. The delivery system of claim 8, wherein the push buttons comprise a pair of push buttons that are configured to be pressed radially inward to release the tip retractor from the handle.

10. The delivery system of claim 6, further comprising a stability shaft surrounding the outer shaft.

11. The delivery system of claim 6, further comprising a prosthetic valve disposed between an outer surface of the inner shaft and an inner surface of the outer shaft.

12. The delivery system of claim 11, wherein the inner shaft includes a reduced diameter portion at a distal portion thereof proximal of the nosecone, wherein the prosthetic valve is disposed around the reduced diameter portion.

* * * * *